United States Patent
Racz

[11] Patent Number: 5,817,074
[45] Date of Patent: Oct. 6, 1998

[54] STELLATE BLOCK NEEDLE

[76] Inventor: Gabor J. Racz, 4412 17th St., Lubbock, Tex. 79416

[21] Appl. No.: 954,543

[22] Filed: Oct. 20, 1997

Related U.S. Application Data

[63] Continuation of Ser. No. 546,997, Oct. 23, 1995, abandoned.

[51] Int. Cl.[6] .................................................... A61M 5/32
[52] U.S. Cl. ............................................ 604/272; 604/264
[58] Field of Search ..................... 604/272, 264, 604/51–53, 158, 164, 170, 171, 239

[56] References Cited

U.S. PATENT DOCUMENTS

| | | |
|---|---|---|
| 2,748,769 | 6/1956 | Huber . |
| 3,076,457 | 2/1963 | Copen . |
| 3,509,880 | 5/1970 | Guttman . |
| 4,240,433 | 12/1980 | Bordow . |
| 4,308,875 | 1/1982 | Young . |
| 4,702,260 | 10/1987 | Wang . |
| 4,722,725 | 2/1988 | Sawyer et al. . |
| 4,838,877 | 6/1989 | Massau ..................... 604/272 |
| 5,019,039 | 5/1991 | Anderson . |
| 5,234,406 | 8/1993 | Kramer et al. . |
| 5,297,546 | 3/1994 | Spofford et al. . |
| 5,478,328 | 12/1995 | Silverman et al. ...................... 604/272 |
| 5,573,519 | 11/1996 | Zohmann ................... 604/272 |

FOREIGN PATENT DOCUMENTS

| | | | |
|---|---|---|---|
| 1142769 | 9/1957 | France ................................ 604/272 |
| 483499 | 7/1953 | Italy . |
| 483499 | 11/1954 | Italy ..................................... 604/272 |

OTHER PUBLICATIONS

Lund, P. C., "Principles and Practice of Spinal Anesthesia,"Charles C. Thomas, Publisher, 1971, pp. 262–295.

*Primary Examiner*—John D. Yasko
*Attorney, Agent, or Firm*—Trask, Britt & Rossa

[57] ABSTRACT

A novel stellate ganglion sympathetic block needle having a side port positioned at a predetermined distance from the needle tip. The novel stellate ganglion sympathetic block needle allows for an effective stellate ganglion sympathetic block even if the needle is placed such that the needle tip opening is under the anterior longitudinal ligament which results in the needle tip opening being constricted, thereby interfering with the injection of the anesthesia. When this interference occurs, the side port of the novel stellate ganglion sympathetic block needle allows directional injection onto the surface of the anterior longitudinal ligament in order to spread onto the surface of the longus coli muscle toward the stellate ganglion, thereby achieving an effective stellate ganglion sympathetic block.

8 Claims, 1 Drawing Sheet

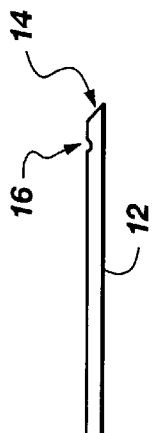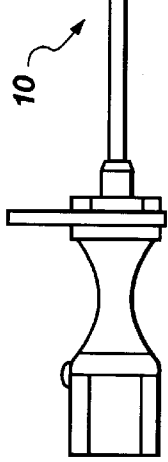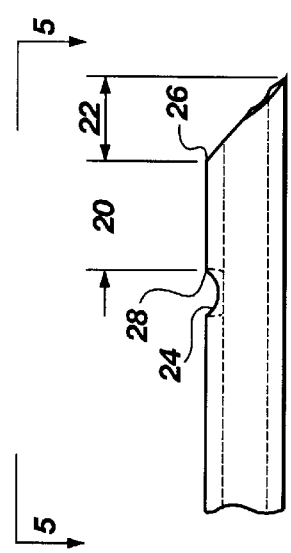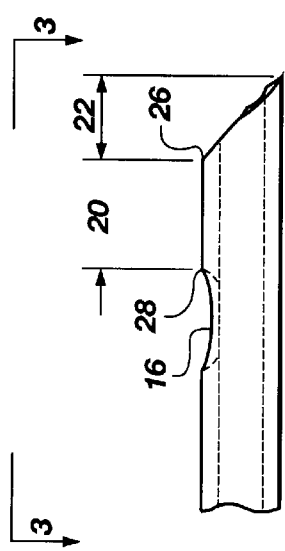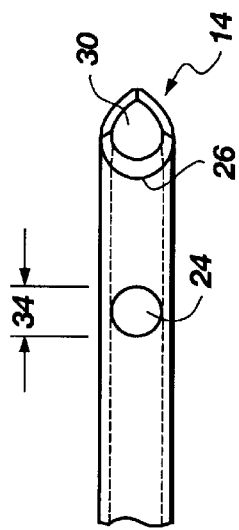

STELLATE BLOCK NEEDLE

This application is a continuation of application Ser. No. 08/546,997, filed Oct. 23, 1995, now abandoned.

FIELD OF THE INVENTION

The present invention relates generally to needles used for aspiration, and more particularly to a needle with a novel side port for performing a stellate ganglion sympathetic block, and its method of use.

BACKGROUND OF THE INVENTION

Needles with orifices located along the length of said needles are known in the art. P. C. Lund, M.D. in his book *Principles and Practices of Spinal Anesthesia*, Charles C. Thomas Books (1971) discloses a variety of needles used for administering spinal anesthesia. The Hingson-Ferguson Spinal Needle (pgs. 280 and 281) and the Lemmon Needle (pgs. 287 and 288) are needles having openings both at the needle tip and along the length of the needle side. This configuration reduces the chance of the inability of administering the anesthesia due to the clogging of the opening at the needle tip.

Needles having a blocked tip with a side opening are used for procedures such as thoracentesis which involves inserting the needle through the thoracic cage into the pleural space between the lung and the chest wall to draw off fluid for diagnostic or therapeutic purposes. Thoracentesis needles generally consist of an orifice free, sharp conical end and a circular side hole for draining fluid.

U.S. Pat. No. 5,019,039 issued May 28, 1991 to R. W. Anderson relates to a fluid drainage needle removably housed within a cannula. The cannula has at least one side opening as well as an opening for the tip of the needle to extend through. The needle and cannula are inserted into the body. The needle is then removed from the cannula which allows fluid to be drained through the cannula.

U.S. Pat. No. 5,271,744 issued Dec. 21, 1993 to Kramer et al. relates to a device for rapid vascular drug delivery, particularly through the adult sternum. The device includes a needle having a slight taper along its length toward a conical, orifice free tip. The conical tip is designed to penetrate bone. The needle taper promotes a good seal between the needle and the bone. The needle has a plurality of orifices located behind the conical tip such that they will not become clogged with bone tissue or the like, thereby allowing the unimpeded delivery of the vascular drug.

A stellate ganglion sympathetic nerve block is the chemical paralysis of the stellate ganglion by a local anesthetic agent injected in the vicinity of the ganglion. When a predetermined amount of blocking agent is correctly injected, the middle cervical ganglion, the intermediate ganglion, the stellate ganglion and the second, third, and fourth thoracic ganglion are anesthetized ("blocked"). Additionally, the superior cervical ganglion is also anesthetized because the nerve fibers which form this ganglion extend through the above-mentioned ganglia. Thus, when a stellate ganglion sympathetic block is correctly executed, the entire cervicothoracic portion of the sympathetic nervous is blocked.

Generally, for short time duration blocks, local anesthetic drugs such as novocaine, pontocaine, xylocaine, metycaime and intracaine, nupercaine, and the like are used. For long time duration blocks, alcohol and phenol are generally used.

When performing a stellate ganglion sympathetic block, a physician relies on superficial landmarks (i.e. bones, cartilage, muscles, tendons, and blood vessels which are near the skin surface) to locate the area of insertion of the needle. Deep landmarks (i.e. bones, periosteum, fascial planes, tendons, and blood vessels) which cannot be seen or palpated can only be felt with the point of the needle. Thus, the accuracy in identifying these deep landmarks depends greatly on the educated touch of the physician.

One of the safest ways to perform a stellate ganglion sympathetic block is to place the patient supine, without a pillow, with the patient's head in a neutral position. While standing on side of the body which is to be block, the physician tactilely locates the cricoid cartilage. The needle is then inserted in a position approximately one finger breadth below the cricoid cartilage, between the carotid sheath and the trachea on the side to be blocked, while aiming slightly medially until the needle makes bony contact with the ventral lateral side of the body of the seventh cervical vertebra (the approximate location of the stellate ganglion). When the needle is in said position, the anesthesia is injected. However, since the inserted location of the needle is a matter of "feel" for the physician, it is common for the needle tip to be placed such that the tip opening is under the anterior longitudinal ligament. This positioning may interfere with injection.

Therefore, it would be advantageous to design a needle which can effectively inject anesthesia during the performance of a stellate ganglion sympathetic block whether or not the needle tip opening is under the anterior longitudinal ligament.

SUMMARY OF THE INVENTION

The present invention eliminates the injection problems during a stellate ganglion sympathetic block by the novel needle opening configuration.

The novel stellate ganglion sympathetic block needle is preferably a standard 20 or 22 gauge needle with a side port positioned at a predetermined distance from the needle tip. Although it is understood that the side port can be placed at any predetermined distance from the needle tip, the preferred distances are 1 mm, 1.5 mm, 2 mm and 4 mm. These distances accommodate the majority of human sizes such that, if the needle tip is constricted, the blocking agent is properly injected in a desired location through the side port. The side port is preferably an oval or a round opening. However, it is understood that the side port could be any shape including square, rectangular, diamond, semi-circle, and the like.

Using the novel stellate ganglion sympathetic block needle begins by placing the patient in a supine position, without a pillow, with the patient's head in a neutral position. While standing on side of the body which is to be blocked, the physician tactilely locates the cricoid cartilage. The needle is then inserted in a position approximately one finger breadth below the cricoid cartilage, between the carotid sheath and the trachea on the side to be blocked, while aiming slightly medially until bony contact is made with the ventral lateral side of the body of the seventh cervical vertebra. When the needle is in said position, the anesthesia is injected. If the needle is in the proper position, the majority of the anesthesia will exit from the needle tip opening. However, if the needle is placed such that the needle tip opening is under the anterior longitudinal ligament, the needle tip opening will be constricted. This constriction usually interferes with the injection of the anesthesia. However, when this interference occurs, the new needle design allows for directional injection out the side port onto the surface of the anterior longitudinal ligament. This allows the anesthesia to spread onto the surface of the longus coli muscle toward the stellate ganglion. Thus, an injection via the side port will achieve an effective stellate ganglion sympathetic block.

BRIEF DESCRIPTION OF THE DRAWINGS

FIG. 1 is a side plan view of the stellate block needle;

FIG. 2 is a side plan view of the tip of the stellate block needle having an oval side port;

FIG. 3 is a top graph view of the tip shown in FIG. 2 along line 3—3;

FIG. 4 is a side plan view of the tip of the stellate block needle having a round side port; and FIG. 5 is a top graph view of the tip shown in FIG. 4 along line 5—5.

DETAILED DESCRIPTION OF THE INVENTION

FIG. 1 illustrates a stellate ganglion sympathetic block needle 10 having an elongate needle portion 12, a needle tip 14, and a side port 16. The elongate needle portion 12 is generally between about 38 mm to 127 mm in length. The stellate ganglion sympathetic block needle 10 is preferably a 20 or 22 gauge needle. The 20 gauge needle has an outside diameter of about 0.0355 to 0.0360 mm and an inside diameter of about 0.0230 to 0.0245 mm. The 22 gauge needle has an outside diameter of about 0.0280 to 0.0205 mm and an inside diameter of about 0.0155 to 0.0170 mm.

As illustrated in FIGS. 2 and 4, the needle tip 14 has a standard needle cut at an angle of 45 degrees which yields a tip length 22 of approximately 0.05055 mm for the 20 gauge needle and approximately 0.03995 mm for the 22 gauge needle. FIGS. 3 and 5 show the side port configuration. The side port 16 is preferably an oval 18 or a round 24 configuration. The oval 18 configuration preferably has a lengthwise diameter 32 of approximately 150% of the inside diameter of the needle 10. The round 24 configuration preferably has a diameter 34 of approximately equal to the inside diameter of the needle 10. It is, of course, understood that the side port could be any shape including square, rectangular, diamond, semi-circle, and the like.

Referring again to FIGS. 2 and 4, side port distance 20 is generally defined as the distance from the needle tip back edge 26 to the edge of the side port 28 nearest the needle tip back edge 26. Although it is understood that the side port 16 can be placed at any predetermined side port distance 20 from the needle tip back edge 26, the preferred side port distances 20 are 1 mm, 1.5 mm, 2 mm and 4 mm. These side port distances 20 accommodate the majority of human sizes such that the blocking agent is properly injected in a desired location through the side port 16.

The stellate ganglion sympathetic block needle 10 is preferably used by inserting said needle 10 in a position approximately one finger breadth below the cricoid cartilage, between the carotid sheath and the trachea on the side to be blocked, aiming slightly medially until bony contact is made with the ventral lateral side of the body of the seventh cervical vertebra. When the needle 10 is in said position, the anesthesia is injected. If the needle 10 is in the proper position, the majority of the anesthesia will exit from the needle tip opening 30. However, if the needle 10 is placed such that the needle tip opening 30 is under the anterior longitudinal ligament, the needle tip opening 30 will be constricted which interferes with the injection of the anesthesia. When this interference occurs, the side port 16 allows directional injection onto the surface of the anterior longitudinal ligament. This allows the anesthesia to spread onto the surface of the longus coli muscle toward the stellate ganglion. Thus, the injection via the side port 16 will still achieve an effective stellate ganglion sympathetic block.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A stellate block needle comprising:

an elongate needle portion having a sharp distal end, an outside diameter of between about 0.0355 to 0.03600 mm and an inside diameter between about 0.0230 to 0.0245 mm;

said elongate needle portion including a first oval aperture sufficient to permit fluid aspiration therethrough formed in the side thereof at a predetermined distance from said distal end, and said elongate needle portion including a second aperture sufficient to permit fluid aspiration therethrough formed through said sharp distal end.

2. A stellate block needle comprising:

an elongate needle portion having a sharp distal end, an outside diameter between about 0.0280 to 0.205 mm and an inside diameter between about 0.0155 to 0.0170 mm;

said elongate needle portion including a first oval aperture sufficient to permit fluid aspiration therethrough formed in the side thereof at a predetermined distance from said distal end, and said elongate needle portion including a second aperture sufficient to permit fluid aspiration therethrough formed through said sharp distal end.

3. A stellate block needle comprising:

an elongate needle portion including a plurality of apertures and a sharp distal end;

a first aperture of said plurality of apertures formed in a side of said elongate needle portion at a predetermined distance from said distal end, having an oval shape with a lengthwise diameter which is about 150% of an inside diameter of said elongate needle portion, and being sufficient to permit fluid aspiration therethrough, and a second aperture of said plurality of apertures being sufficient to permit fluid aspiration therethrough formed through said sharp distal end.

4. A stellate block needle comprising:

an elongate needle portion having a sharp distal end, said elongate needle portion including a first round aperture sufficient to permit fluid aspiration therethrough formed in its side at a predetermined distance from said distal end and having a diameter that is about equal to an inside diameter of the needle, and said elongate needle portion including a second aperture sufficient to permit fluid aspiration therethrough formed through said sharp distal end.

5. A stellate block needle comprising:

an elongate needle portion having a sharp distal end;

said elongate needle portion including an oval first aperture sufficient to permit fluid aspiration therethrough formed in its side at a predetermined distance from said distal end, said predetermined distance being selected from the group consisting of 1 mm, 1.5 mm, 2 mm and 4 mm, and said elongate needle portion including a second aperture sufficient to permit fluid aspiration therethrough formed through said sharp distal end.

6. A stellate block needle comprising:

an elongate needle portion having an outside diameter between about 0.0355 to 0.0360 mm, an inside diameter between about 0.0230 to 0.0245 mm, and including a beveled sharp distal end with a back edge proximal to said distal end, said elongate needle portion including a first oval aperture sufficient to permit fluid aspiration therethrough formed in its side at a predetermined distance from said back edge and positioned on the same side of said elongate needle portion as the most proximal point of said back edge, and said elongate needle portion including a second aperture sufficient to permit fluid aspiration therethrough formed through said sharp distal end.

7. A stellate block needle comprising:

an elongate needle portion having an outside diameter between about 0.0280 to 0.0205 mm, an inside diameter between about 0.0155 to 0.0170 mm, and including a beveled sharp distal end with a back edge proximal to said distal end, said elongate needle portion including a first oval aperture sufficient to permit fluid aspiration therethrough formed in its side at a predetermined distance from said back edge and positioned on the same side of said elongate needle portion as the most proximal point of said back edge, and said elongate needle portion including a second aperture sufficient to permit fluid aspiration therethrough formed through said sharp distal end.

8. A stellate block needle comprising:

an elongate needle portion including a beveled sharp distal end with a back edge proximal to said distal end, said elongate needle portion including a first oval aperture sufficient to permit fluid aspiration therethrough formed in its side at a predetermined distance from said back edge and said first aperture being positioned on the same side of said elongate needle portion as the most proximal point of said back edge, said first oval aperture having a lengthwise diameter which is about 150% of an inside diameter of the needle, and said elongate needle portion including a second aperture sufficient to permit fluid aspiration therethrough formed through said sharp distal end.

\* \* \* \* \*

UNITED STATES PATENT AND TRADEMARK OFFICE
CERTIFICATE OF CORRECTION

PATENT NO.  : 5,817,074
DATED       : October 6, 1998
INVENTOR(S) : Gabor C. Racz It is certified that error appears in the above-identified patent and that said Letters Patent is hereby corrected as shown below:

On the title page, under "[56] References Cited, U.S. PATENT DOCUMENTS", add --5,234,406    8/1993    Drasner et al.-- ;

"5,234,406    8/1993    Kramer, et al" should read --5,271744 12/1993 Kramer, et al.

On the title page, under "[57] ABSTRACT", line 5, after "block", insert a comma --,--.

Signed and Sealed this

Tenth Day of August, 1999

Q. TODD DICKINSON

*Attest:*

*Attesting Officer*                Acting Commissioner of Patents and Trademarks

UNITED STATES PATENT AND TRADEMARK OFFICE
CERTIFICATE OF CORRECTION

PATENT NO. : 5,817,074
DATED : October 6, 1998
INVENTOR(S) : Gabor J. Racz

It is certified that error appears in the above-identified patent and that said Letters Patent is hereby corrected as shown below:

Column 4,
Line 28, change "0.205" to -- 0.0205 --.

Signed and Sealed this

Twenty-seventh Day of December, 2005

JON W. DUDAS
*Director of the United States Patent and Trademark Office*